(12) United States Patent
Nottebaum et al.

(10) Patent No.: US 7,957,916 B2
(45) Date of Patent: Jun. 7, 2011

(54) METHODS, SYSTEMS, AND COMPUTER PROGRAM PRODUCTS FOR PRODUCING THEORETICAL MASS SPECTRAL FRAGMENTATION PATTERNS OF CHEMICAL STRUCTURES

(75) Inventors: Lynde J. Nottebaum, San Diego, CA (US); Thomas D. McClure, La Jolla, CA (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 12/695,310

(22) Filed: Jan. 28, 2010

(65) Prior Publication Data
US 2010/0138206 A1    Jun. 3, 2010

Related U.S. Application Data

(62) Division of application No. 11/112,957, filed on Apr. 22, 2005, now Pat. No. 7,801,684.

(51) Int. Cl.
*G01N 31/00* (2006.01)
*G06F 17/10* (2006.01)
(52) U.S. Cl. .............................. 702/22; 702/19; 703/2
(58) Field of Classification Search .................. None
See application file for complete search history.

(56) References Cited

U.S. PATENT DOCUMENTS

| 5,538,897 | A | 7/1996 | Yates et al. | |
|---|---|---|---|---|
| 6,017,693 | A | 1/2000 | Yates et al. | |
| 6,584,412 | B1 | 6/2003 | Brecher | |
| 2004/0088118 | A1* | 5/2004 | Jensen et al. | 702/30 |
| 2005/0228592 | A1* | 10/2005 | Ahuja et al. | 702/19 |

OTHER PUBLICATIONS

Hugo Kubinyi, "Combinatorial and computational approaches in structure-based drug design," Current Opinion in Drug Discovery and Development, vol. 1 (1998), pp. 16-27.*

Eng et al., An approach to correlate tandem mass spectral data of peptides with animo acid sequences in a protein database, American Society for Mass Spectrometry, 5:976-989, 1994.

* cited by examiner

*Primary Examiner* — Marjorie Moran
*Assistant Examiner* — Anna Skibinsky
(74) *Attorney, Agent, or Firm* — Bruce Vrana (57) ABSTRACT

Methods, systems, and computer program products for generating theoretical mass spectral fragmentation patterns of a chemical structure is provided. The method includes obtaining a description of a chemical structure and generating, from the description, a list of chemical structure information. A binary tree data structure is used to organize the list of chemical structure information. The binary tree data structure may be fragmented by determining, based on a set of predetermined rules, a fragmentation point between two nodes in the binary tree data structure thereby dividing the binary tree data structure into a fragment and a complement. The molecular formula and molecular weight of each fragment is determined. The binary tree data structure is traversed and appropriate fragmentation rules are applied to produce a plurality of theoretical molecular fragments.

16 Claims, 9 Drawing Sheets

```
1   phenacetin.mol
2     ChemDraw05010315572D          } header block
3
4    13 13  0  0  0  0  0  0  0  0999 V2000
5      0.7145  -0.4125   0.0000 C   0  0  0  0  0  0  0  0  0  0  0  0
6      0.7145   0.4125   0.0000 C   0  0  0  0  0  0  0  0  0  0  0  0
7      0.0000   0.8250   0.0000 C   0  0  0  0  0  0  0  0  0  0  0  0
8     -0.7145   0.4125   0.0000 C   0  0  0  0  0  0  0  0  0  0  0  0
9     -0.7145  -0.4125   0.0000 C   0  0  0  0  0  0  0  0  0  0  0  0
10     0.0000  -0.8250   0.0000 C   0  0  0  0  0  0  0  0  0  0  0  0
11    -1.4289   0.8250   0.0000 O   0  0  0  0  0  0  0  0  0  0  0  0    atom block
12     1.4289  -0.8250   0.0000 N   0  0  0  0  0  0  0  0  0  0  0  0
13    -2.1434   0.4125   0.0000 C   0  0  0  0  0  0  0  0  0  0  0  0
14    -2.8579   0.8250   0.0000 C   0  0  0  0  0  0  0  0  0  0  0  0
15     2.1434  -0.4125   0.0000 C   0  0  0  0  0  0  0  0  0  0  0  0
16     2.1434   0.4125   0.0000 O   0  0  0  0  0  0  0  0  0  0  0  0
17     2.8579  -0.8250   0.0000 C   0  0  0  0  0  0  0  0  0  0  0  0
18    1  2  2  0
19    1  6  1  0
20    1  8  1  0
21    2  3  1  0
22    3  4  2  0
23    4  5  1  0
24    4  7  1  0      bond block
25    5  6  2  0
26    7  9  1  0
27    8 11  1  0
28    9 10  1  0
29   11 12  2  0
30   11 13  1  0
31   M  END
```

METHODS, SYSTEMS, AND COMPUTER PROGRAM PRODUCTS FOR PRODUCING THEORETICAL MASS SPECTRAL FRAGMENTATION PATTERNS OF CHEMICAL STRUCTURES

CROSS REFERENCE TO RELATED APPLICATIONS

This application is a divisional of U.S. patent application Ser. No. 11/112,957, filed Apr. 22, 2005 now U.S. Pat. No. 7,801,684, the disclosure of which is incorporated herein by reference in its entirety.

TECHNICAL FIELD

The presently disclosed subject matter relates to methods and computer program products for identifying the structure of molecules processed using mass spectrometry. More particularly, the presently disclosed subject matter relates to methods and computer program products for identifying chemical compounds based on an automated comparison of experimentally generated mass spectrometry data from the compound or compounds of interest with a database of theoretically generated mass spectra. The presently disclosed subject matter also relates to methods and computer program products for generating the database of theoretical mass spectra.

BACKGROUND ART

Mass spectrometry is an analytical technique for the determination of molecular weight related information and in some instances structurally significant fingerprint information from molecular fragments, all toward the identification of chemical structures, the determination of the composition of mixtures, and qualitative elemental analysis. In operation, a mass spectrometer generates ions from sample molecules under investigation (the analyte), separates the ions according to their mass-to-charge ratio (m/z), and measures the relative abundance of each ion. In a typical mass spectrometer, the path of travel of the Ions through the mass spectrometer depends on their mass and charge, thus ions are separated based upon their m/z and then detected. The detector within the mass spectrometer produces a relative m/z value along with a measure of signal intensity related to the number of ions of the same m/z value that are detected. A plot of the signal intensity values as a function of the m/z value is known as a mass spectrum.

If the analyte remains intact throughout this process, data obtained will be related to the molecular weight for the entire intact analyte ion. Typically, however, and especially for the case of larger analytes, it is beneficial to obtain data corresponding to the molecular weight of various fragments of the analyte. The resulting spectrum is known as a fragmentation spectrum for the analyte of interest.

Although the fragmentation spectrum can be of interest for a variety of uses, it is often desired to use the fragmentation spectrum as a molecular "finger-print" to identify a compound or compounds of interest that resulted in the fragmentation mixture. Previous approaches have typically involved using the fragmentation spectrum as a basis for hypothesizing one or more candidate compounds. This procedure has typically involved manual analysis by a skilled researcher.

The procedure that involves hypothesizing identification of candidate compounds based on direct analysis of experimental fragmentation spectra is useful in a number of contexts, but also has certain difficulties. For example, manual interpretation of the fragmentation spectra so as to identify unknown analytes is time-consuming, often inaccurate, and highly technical and in general can be performed only by those with extensive experience in mass spectrometry. Reliance on human interpretation often means that analysis is relatively slow and lacks strict objectivity.

Alternatively, it is also possible to utilize a system for correlating fragment spectra from unknown analytes with known compound fragment spectra derived from a library of fragment spectra from previously analyzed known compounds. Such a system may avoid the delay and/or subjectivity involved in hypothesizing or deducing candidate amino acid sequences from the fragmentation spectra.

Although comparing experimental fragment spectra with a database of known compound spectra is an improvement over direct analysis of the experimental spectra, this process can also have certain drawbacks. For example, the database of known spectra must usually be accumulated through mass spectrometry analysis of each of the compounds included in the database. Therefore, establishing the database initially and updating it requires expenditure of time and resources for derivation of the database spectra. Further, it may also be difficult to obtain fragmentation spectra on some compounds desirable to include in the database, if, for example, the compounds could not be readily purified or obtained in sufficient quantities necessary for mass spectrometry. Finally, comparative analysis of experimental fragmentation spectra to the database spectra must be performed, which again requires extensive time and resources. These drawbacks are particularly acute when large numbers of unknown compounds must be identified rapidly, for example, in high throughput screening procedures for identification of potential drug candidates.

Therefore, it would be desirable to quickly and efficiently identify unknown analytes by comparing and matching mass spectrometry fragmentation data with a database of fragmentation spectra from known compounds. It would further be desirable to be able to quickly and efficiently populate the database of fragmentation spectra without necessarily analyzing each compound by mass spectrometry in order to derive the fragmentation spectra.

SUMMARY

A method for generating theoretical mass spectral fragmentation patterns of a chemical structure is provided. The method includes obtaining a description of a chemical structure and generating, from the description, a list of chemical structure information. A binary tree data structure is used to organize the list of chemical structure information. The binary tree data structure may be fragmented by determining, based on a set of predetermined rules, a fragmentation point between two nodes in the binary tree data structure, thereby dividing the binary tree data structure into a fragment and a complement. The molecular formula and molecular weight of each fragment is determined. The binary tree data structure is traversed and appropriate fragmentation rules are applied to produce a plurality of theoretical molecular fragments.

DETAILED DESCRIPTION

The subject matter described herein provides methods for producing theoretical mass spectral fragmentation patterns of chemical structures. The theoretical mass spectra can then be incorporated into one or more databases. The subject matter described herein further provides methods for identifying one or more unknown analytes by comparing and matching the theoretical spectra within the one or more databases with experimentally derived mass spectra of the analytes in order to identify or otherwise characterize the one or more unknown analytes.

It should be appreciated that the methods described herein may be executed manually or with the assistance of a computer program. As such, the method is described in terms of the application of rule sets that may be applied manually or converted, by one skilled in the art of computer programming, into a sequence of computer-executable instructions. The computer-executable instructions may be embodied in a computer-readable medium. Exemplary computer-readable media suitable for implementing the methods described herein include electrical, optical, and magnetic memory storage devices and downloadable electrical signals. The computer-readable medium may contain sets of instructions that implement functions, modules, or processes for producing theoretical mass spectral fragmentation patterns of chemical structures. The terms "function", "module", and "process" are used interchangeably herein and are intended to refer to a set of computer-executable instructions for implementing portions of the methods for producing theoretical mass spectral fragmentation patterns of chemical structures described herein.

Figure 1:
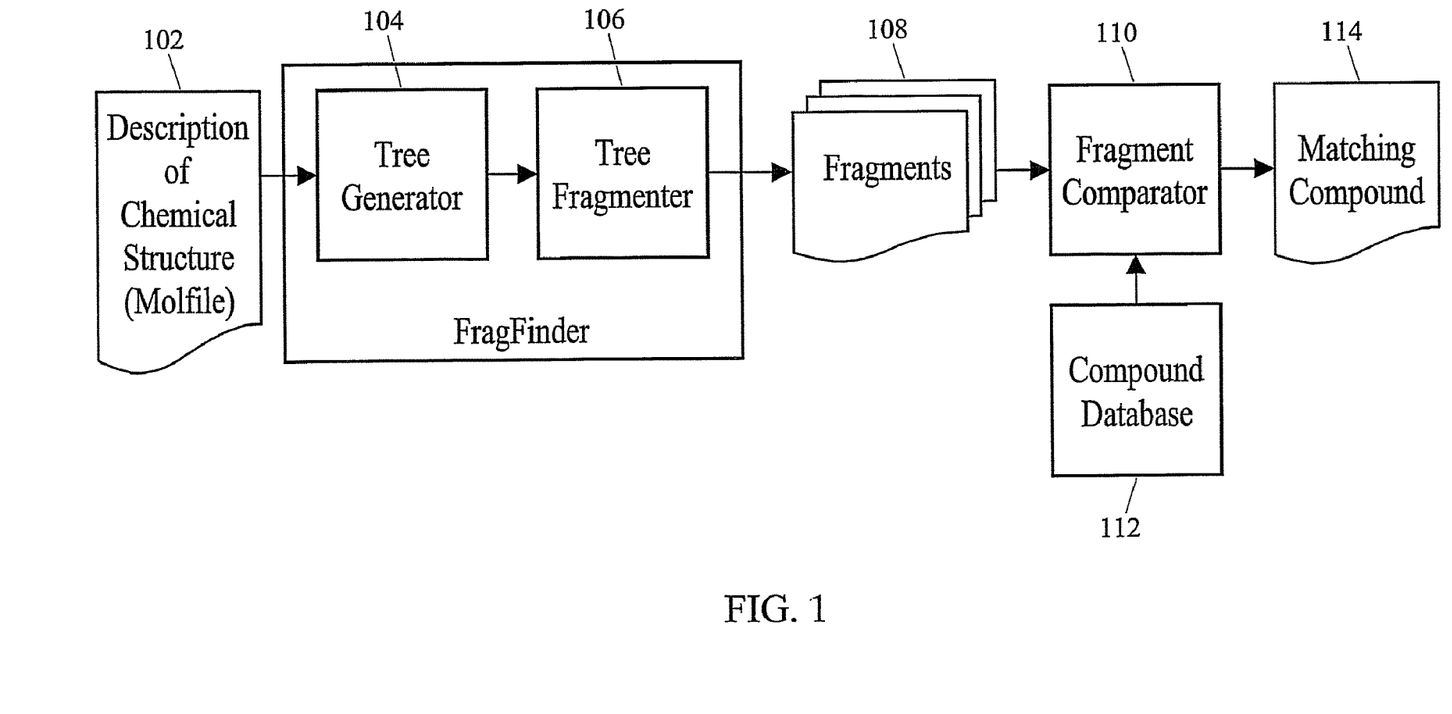
FIG. 1 is a block diagram of a system for modeling a chemical structure and producing theoretical mass spectral fragmentation patterns of the chemical structure in accordance with the subject matter described herein.

FIG. 1 is a block diagram of a system for modeling a chemical structure and producing theoretical mass spectral fragmentation patterns of the chemical structure in accordance with the subject matter described herein. A description 102 of the chemical structure of interest is used as input to a tree generation process 104, which creates a binary tree representing the chemical structure. The binary tree is input to a tree fragmentation process 106, where a predetermined set of rules are applied to the binary tree structure to produce one or more tree fragments 108. Fragment comparator 110 compares each tree fragment 108 to compounds found in a compound database 112. Based the comparison, an identity of a matching compound 114 may be found.

Description 102 of the chemical structure of interest may be created, for example, by drawing the chemical structure using a commercially available software package, such as ChemDraw by CambridgeSoft Corporation, Cambridge, Mass., USA and storing description 102 of the chemical structure in a chemical table file, such as a molfile. Exemplary content and structure of a molfile will be described in detail below.

Figure 2:
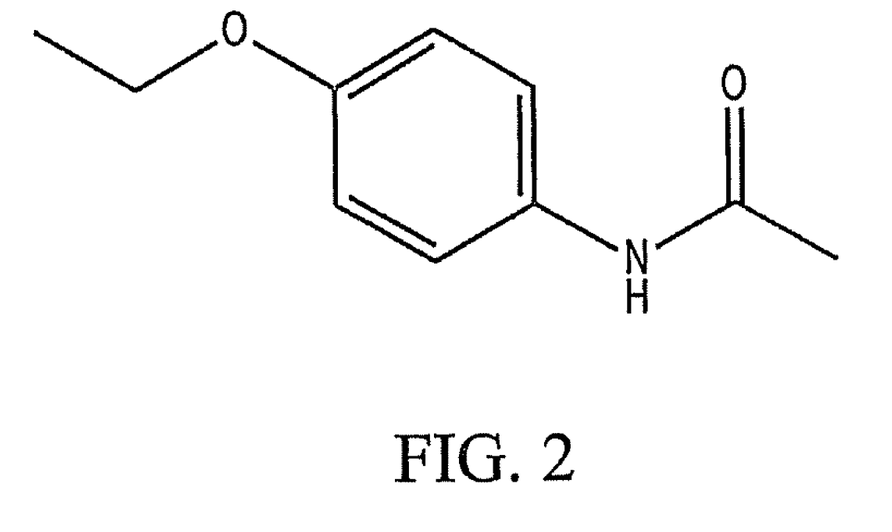
FIG. 2 is a diagram of the chemical structure of phenacetin.

FIG. 2 is a diagram of the chemical structure of phenacetin (N-[4-ethoxyphenyl]acetamide; acetophenetidin), which will be used as one example to illustrate various aspects of the subject matter described herein. It should be appreciated that the subject matter described herein is not limited to analysis of any particular chemical structure or to a chemical structure having any particular structural elements. One skilled in the art would appreciate that atoms not explicitly labeled in FIG. 2 are carbon atoms and each of the carbon atoms may be bonded to an appropriate number of hydrogen atoms, which are also not shown.

Figure 3:
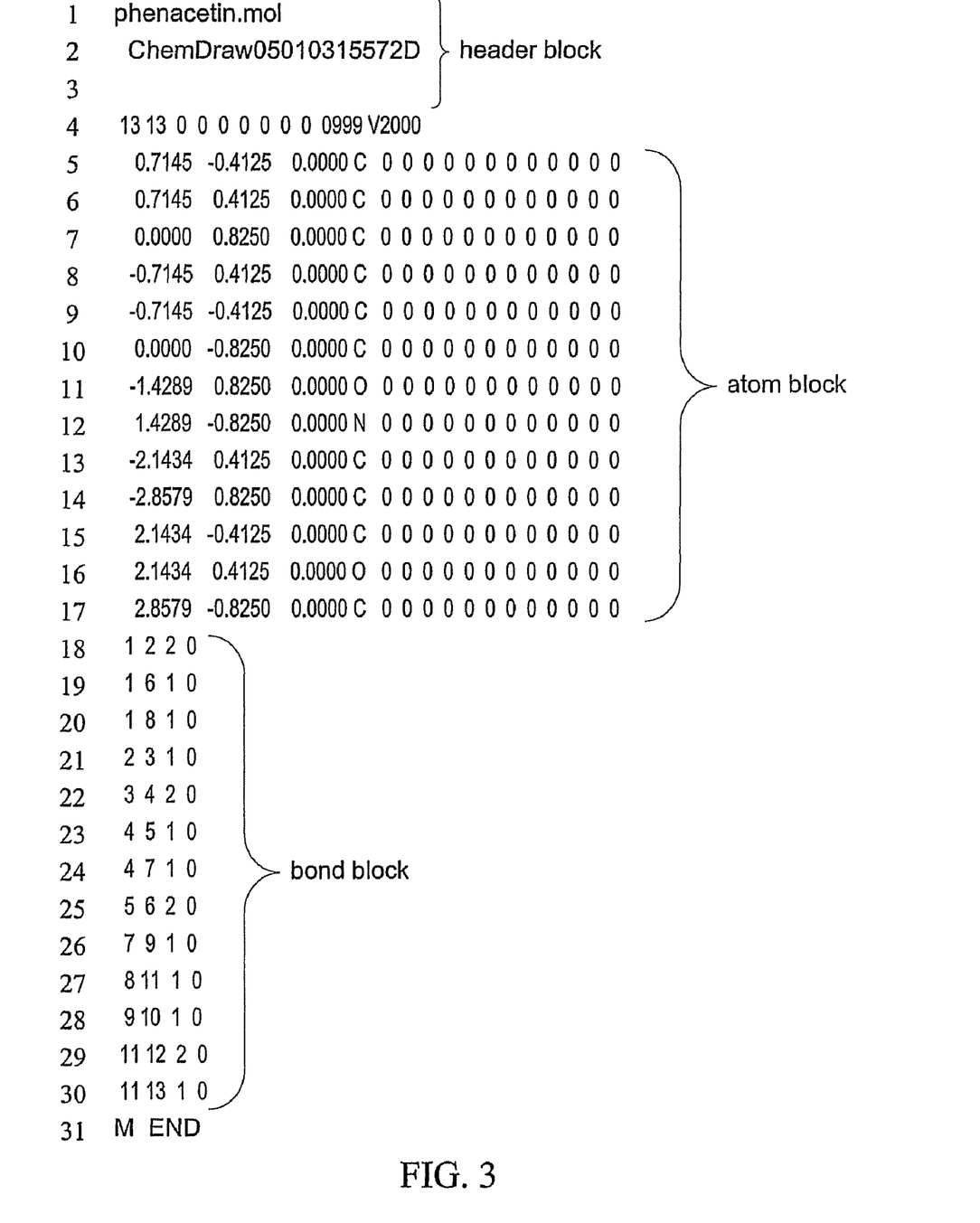
FIG. 3 is a listing of a molfile for phenacetin.

FIG. 3 is a listing of a molfile for phenacetin generated by ChemDraw. Line numbers have been added to FIG. 3 to assist in referencing portions of the listing, but are not a part of the molfile file structure. The molfile file structure is defined by MDL Information Systems, Inc., and is used by various commercial software and research databases to store chemical structure information. With reference to FIG. 3, lines 1-3 form a header block and contain information such as the name of the molfile, the name of the software program used to create the molfile, and other information and comments. Lines 4-31 form the connection table, which describes the structure of phenacetin. For example, line 4 includes, among other things, the number of atoms in the structure and the number of bonds in the structure. Lines 5-17 form the atom block and list each atom in the structure, including the graphical coordinates of the atom, atom name, and properties of the atom in the structure, including charge, valance, and difference in mass from that specified in the periodic table. Lines 18-30 form the bond block and list each bond in the structure, including numerical references to the two bonded atoms and a bond type indicator. The numerical references used to identify the bonded atoms in the bond list entry correspond to the placement of the referenced atoms in the atom block. For example, line 18 indicates a bond between atom #1 (line 5) and atom #2 (line 6) and indicates that the bond between the two carbon atoms is a double bond. Although not shown in FIG. 3, the molfile may include additional blocks that reflect other properties of the chemical structure. In FIG. 3, line 31 marks the end of the molfile.

Figure 4:
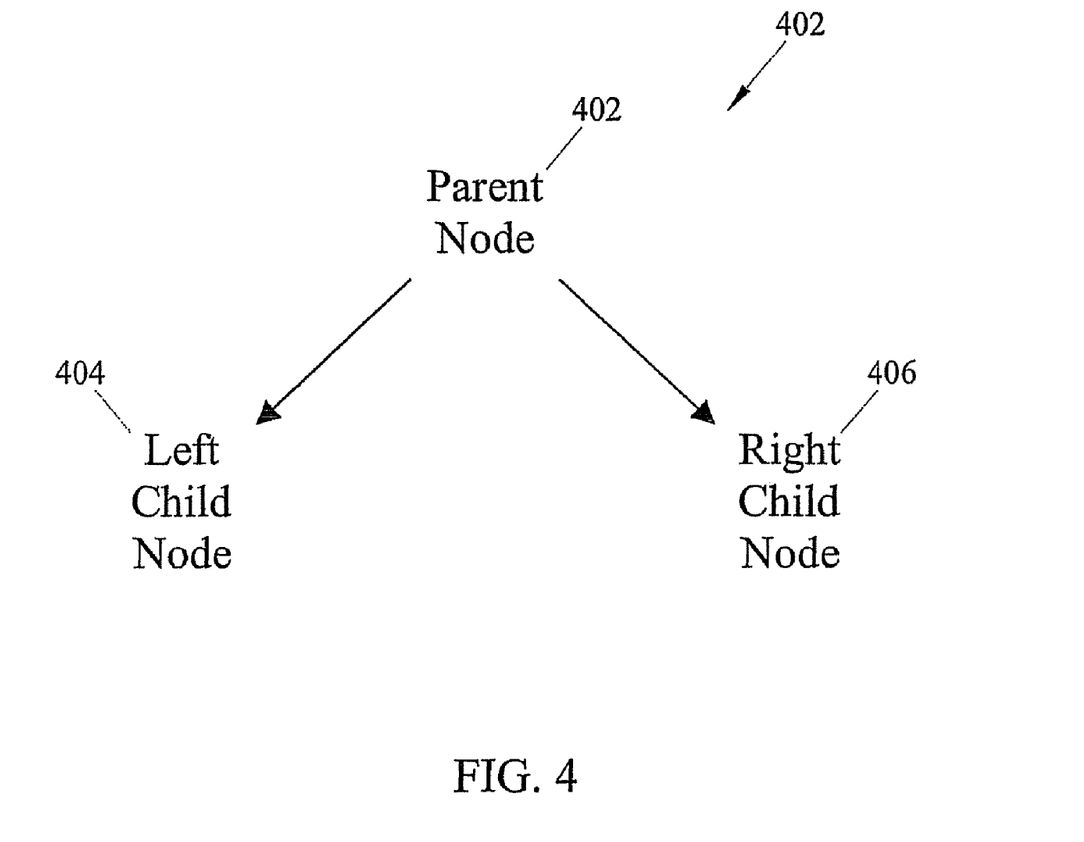
FIG. 4 is a diagram of the primary elements of a binary tree structure.

The information contained in the molfile is used to generate a binary tree structure that represents the relationship between the atoms of the chemical structure. FIG. 4 is a diagram of the primary elements of a binary tree structure 400. A binary tree includes a parent node 402 and up to two child nodes 404 and 406. Child nodes 404 and 406 are referred to as either a left-child node 404 or a right-child node 406. Binary tree structure 400 may be formed in stages, with a child node in one stage acting as a parent node for a subsequent stage. The top-most node in the tree structure, which does not have a parent node, is referred to as the root node. All other nodes in the tree have one parent node.

In accordance with an aspect of the subject matter described herein, each node in the binary tree structure 400 may be one of four node types: an atom node, a ringframe node, a branch node, and a ring node. Two node types, the atom node and the ringframe node, may represent elements of the chemical structure being modeled. For example, an atom node may represent an atom in the chemical structure and a ringframe node may represent a ring in the chemical structure. A branch node may represent a branch in the tree structure from one atom to another non-child atom. A ring node may identify the ring structure. As described in greater detail below and in accordance with one aspect of the subject matter described herein, a rule set governs the placement of node types in the tree structure.

An exemplary tree building process begins by generating a list of molecular structure information derived from the molfile. These lists include an atom list, a ring list, and a chain list. Table 1 is an exemplary atom list for phenacetin.

TABLE 1

Atom List for Phenacetin

| Atom # | Atom Name | Bond List | In a Ring? | Ring List | Node List |
|---|---|---|---|---|---|
| 1 | C | 2, 6, 8 | yes | 1 | 0x002F6618 |
| 2 | C | 1, 3 | yes | 1 | 0x002F6998 |
| 3 | C | 2, 4 | yes | 1 | 0x002F6B50 |
| 4 | C | 3, 5, 7 | yes | 1 | 0x002F6218, 0x002F6BB8 |
| 5 | C | 4, 6 | yes | 1 | 0x002F66C8 |
| 6 | C | 1, 5 | yes | 1 | 0x002F6730 |
| 7 | O | 4, 9 | no | — | 0x002F5D88 |
| 8 | N | 1, 11 | no | — | 0x002F68E8 |
| 9 | C | 7, 10 | no | — | 0x002F5DF0 |
| 10 | C | 9 | no | — | 0x002F5EA0 |
| 11 | C | 8, 12, 13 | no | — | 0x002F6AA0 |
| 12 | O | 11 | no | — | 0x002F8DA0 |
| 13 | C | 11 | no | — | 0x002F8F10 |

In Table 1, the atom list includes an entry for each atom listed in the atom block of the molfile. Each entry includes the atom number, atom name, a bond list (derived from the bond block of the molfile) containing a list of atoms sharing bonds with the atom, and, if the atom belongs to a ring, a list of rings to which the atom belongs. As previously noted, it may be desirable to implement various aspects of the subject matter described herein as computer-executable instructions. In an embodiment of the subject matter described herein, a data structure is used to represent each entry in the atom list of Table 1. The data structure may be defined in C or C++ as follows.

```
typedef struct_atom
{
    int         nAtomNumber;    // atom number
    CString     sAtomName;      // atom name
    bool        bRing;          // true if ring member
    BONDLIST    vecBond;        // list of atom bonds
    NLIST       vecRingNumber;  // list of member rings
    NODELIST    vecNode;        // list of tree nodes
} Atom;
```

The data structure includes six elements: the atom number (nAtomNumber), atom name (sAtomName), a flag indicating whether the atom is a member of a ring (bRing), a list of atoms sharing bonds with the atom (vecBond), a list of rings that the atom is a member of (vecRingNumber), and a list of tree nodes created to represent the atom (vecNode). The node list is empty until the tree structure is built, as described below.

Table 2 is an exemplary ring list for phenacetin. The ring list includes an entry for each ring in the chemical structure. Each entry includes a list of atoms that form the ring. It should be appreciated that not all chemical structures include rings. Thus, the ring list may be empty.

TABLE 2

Exemplary Ring List for Phenacetin

| Ring # | Atoms in Ring | RingFrame Node |
|---|---|---|
| 1 | 1, 2, 3, 4, 5, 6 | 0x002F62C8 |

In an embodiment of the subject matter described herein, a data structure is used to represent each entry in the ring list of Table 2. The data structure may be defined in C or C++ as follows.

```
typedef struct_ringinfo
{
    int         nRingNumber;    // ring number
    NLIST       vecRing;        // ring list
    TreeNode*   pRingFrame;     // pointer to ringframe
                                // node
} RingInfo;
```

The data structure includes three elements: the ring number (nRingNumber), a list of atoms that form the ring (vecRing), and a pointer to the ringframe node that represents the ring in the tree (pRingFrame). The ringframe node pointer may be set to NULL until the tree structure is built, as described below.

Table 3 is an exemplary chain list for phenacetin. The chain list includes a single entry and lists the atoms that form the longest chain of non-ring atoms in the chemical structure. The chain list may be empty, for example, if the chemical structure consists primarily of ring systems.

TABLE 3

Exemplary Chain List for Phenacetin
Atoms in Chain

| 7, 9, 10 |
|---|

Once the atom list, ring list, and chain list have been built, the process of building the corresponding tree structure begins. As noted above, a rule set governs the placement of node types in the tree structure. The tree structure is based on a tree frame, which is a chain of nodes that, starting from the root node, are linked via right-child node relationships. Beginning with the root node and working through each node in the tree frame, other nodes or subtrees are added to the tree structure until each atom in the chemical structure is represented by a node in the tree structure. In an embodiment of the subject matter described herein, a data structure may be used to represent each tree node. The data structure may be defined in C or C++ as follows.

```
typedef struct treenode
{
    CString sName;          // node item name
    int     nType;          // node type
    int     nNumber;        // node number
    int     nRingNumber;    // ring number if item
                            // belongs to a ring
    int     nLeftBond;      // bond with left child
    int     nRightBond;     // bond with right child
```

-continued

| | | |
|---|---|---|
| bool | bRingProxy; | // true if atom node<br>// that is a ring proxy |
| int | nFragType; | // fragment type; set<br>// during tree traversal |
| treenode* | left; | // pointer to left child<br>// node |
| treenode* | right; | // pointer to right child<br>// node |
| treenode* | parent; | // pointer to parent<br>// node |
| } TreeNode; | | |

The data structure includes 11 elements: the type of node (nType), such as atom, branch, ring, or ringframe; the node name (sName) and number (nNumber); the number of the ring that the node belongs to, of any (nRingNumber); the type of bond with left (nLeftBond) and right (nRightBond) child, such as single, double, or triple; a flag indicating if the node is a ring proxy atom node (bRingProxy); pointers to the parent node, the left-child node and the right-child node of the current node; and a fragment type flag (nFragType), which is set/reset many times during tree traversal, as described in greater detail below.

Figure 5A:
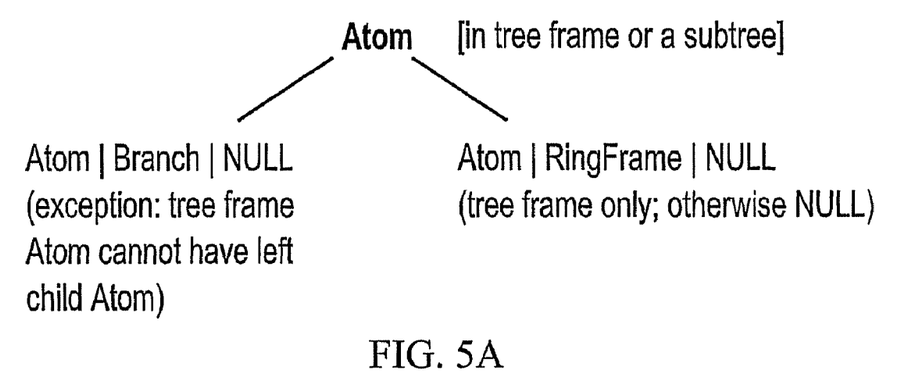
FIG. 5A is a diagram depicting the valid child node types for a parent atom node.

FIGS. 5A-5D summarize the placement rules for the various node types. FIG. 5A is a diagram depicting the valid child node types for a parent atom node. The atom node may appear in either the tree frame or in a subtree. If the atom node is in the tree frame, then the right-child node, if present, may be either an atom node or a ringframe node, and the left-child node, if present, may be a branch node only. If the atom node is not in the tree frame (i.e., the atom node is in a subtree), then the left-child node, if present, may be either an atom node or a branch node. An atom node in a subtree cannot have a right-child node.

Figure 5B:
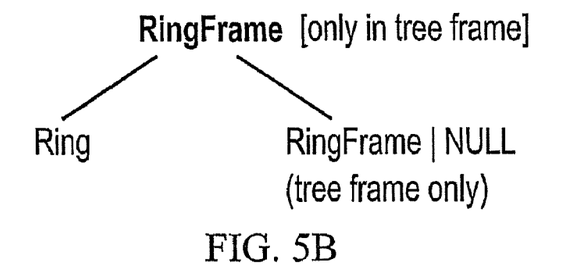
FIG. 5B is a diagram depicting the valid child node types for a parent ringframe node.

FIG. 5B is a diagram depicting the valid child node types for a parent ringframe node. The ringframe node may appear in the tree frame only. The ringframe node will always have a ring node as the left-child node, and the right-child node, if present, may be a ringframe node.

Figure 5C:
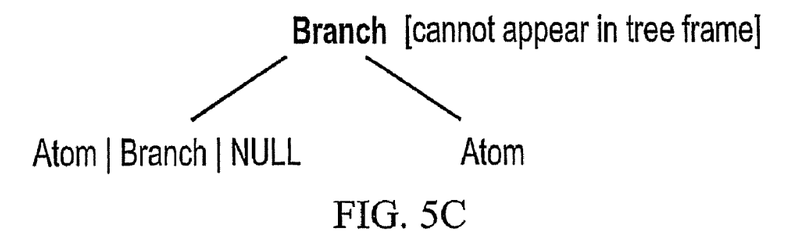
FIG. 5C is a diagram depicting the valid child node types for a parent branch node.

FIG. 5C is a diagram depicting the valid child node types for a parent branch node. The branch node cannot appear in the tree frame. The right-child node is an atom node and the left-child node, if present, may be either an atom node or a branch node.

Figure 5D:
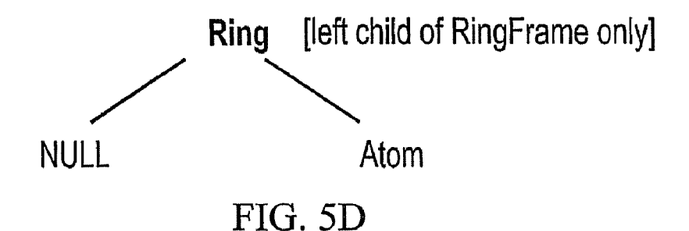
FIG. 5D is a diagram depicting the valid child node types for a parent ring node.

FIG. 5D is a diagram depicting the valid child node types for a parent ring node. The ring node only appears as the left-child node of a ringframe node and always has an atom node as its right-child node. The ring node does not have a left-child node.

Applying the node placement rules, the tree frame may be built from atom nodes and/or ringframe nodes, with atom nodes, if present, filling the initial positions of the tree frame followed by any ringframe nodes. In an embodiment of the subject matter described herein, the tree frame is built using atom nodes representing each atom in the chain list. If the chain list is empty, the tree frame is built using ringframe nodes representing each ring in the ring list.

Figure 6:
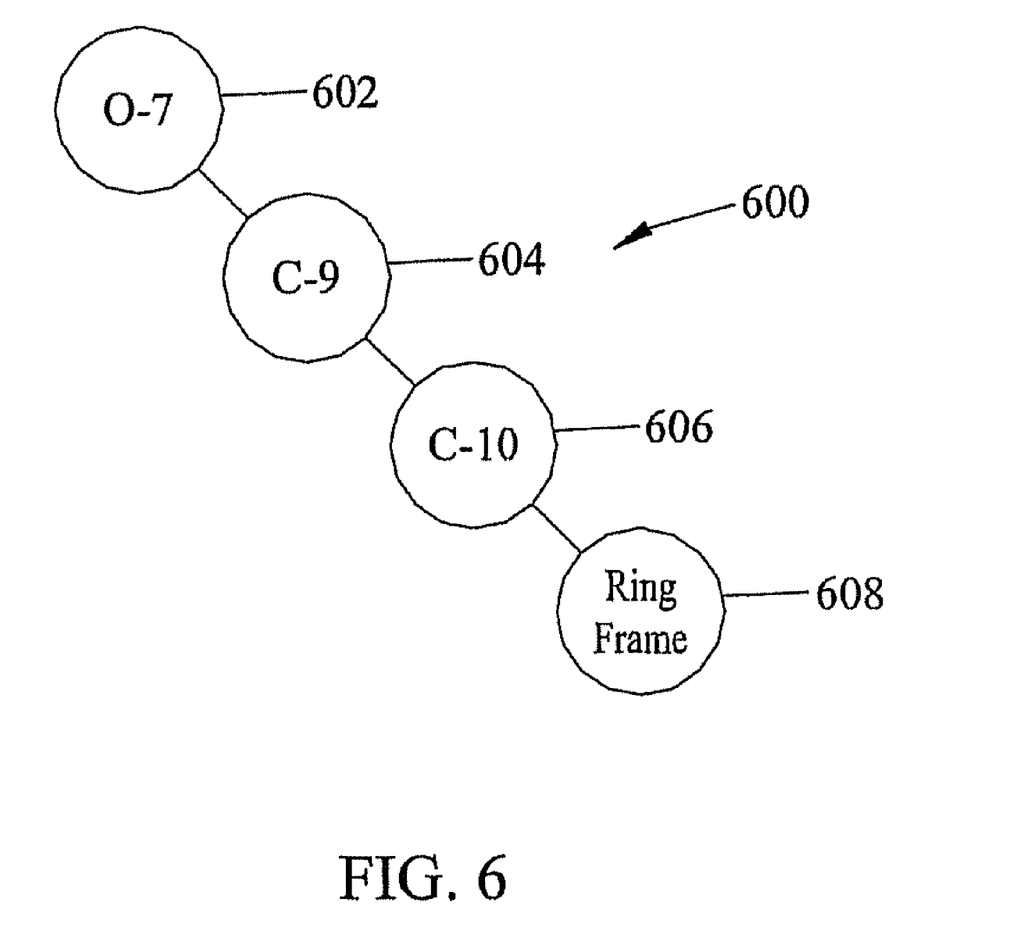
FIG. 6 is a diagram of a tree frame for phenacetin.

FIG. 6 is a diagram of a tree frame for phenacetin. The tree frame 600 includes three atom nodes 602, 604, and 606 and a ringframe node 608. In FIG. 6, each atom node 602, 604, and 606 is labeled with the atom name and number as it is listed in Table 1. Atom node 602 is the root node of the tree structure and is the parent node of atom node 604. Atom node 604 is the right-child node of atom node 602 and the parent node of atom node 606. Atom node 606 is the right-child node of atom node 604 and the parent node of ringframe node 608.

Once the tree frame 600 is built, the atom list and ring list are used to populate the left subtree of each node in the tree frame 600. For each atom node in the tree frame 600, a left subtree is generated by examining the atom's connectivity list and generating branch subtrees for each atom not already connected in the tree. If the atom is connected to a ring, a ring-proxy atom node is created in the branch subtree and indicates a point at which a non-ring atom is connected to a ring. A ringframe node associated with the ring-proxy atom node may be added to the tree frame 600 if, for example, the ring associated with the ring-proxy atom node is not already represented in the tree frame 600 by a ringframe node.

Figure 7:
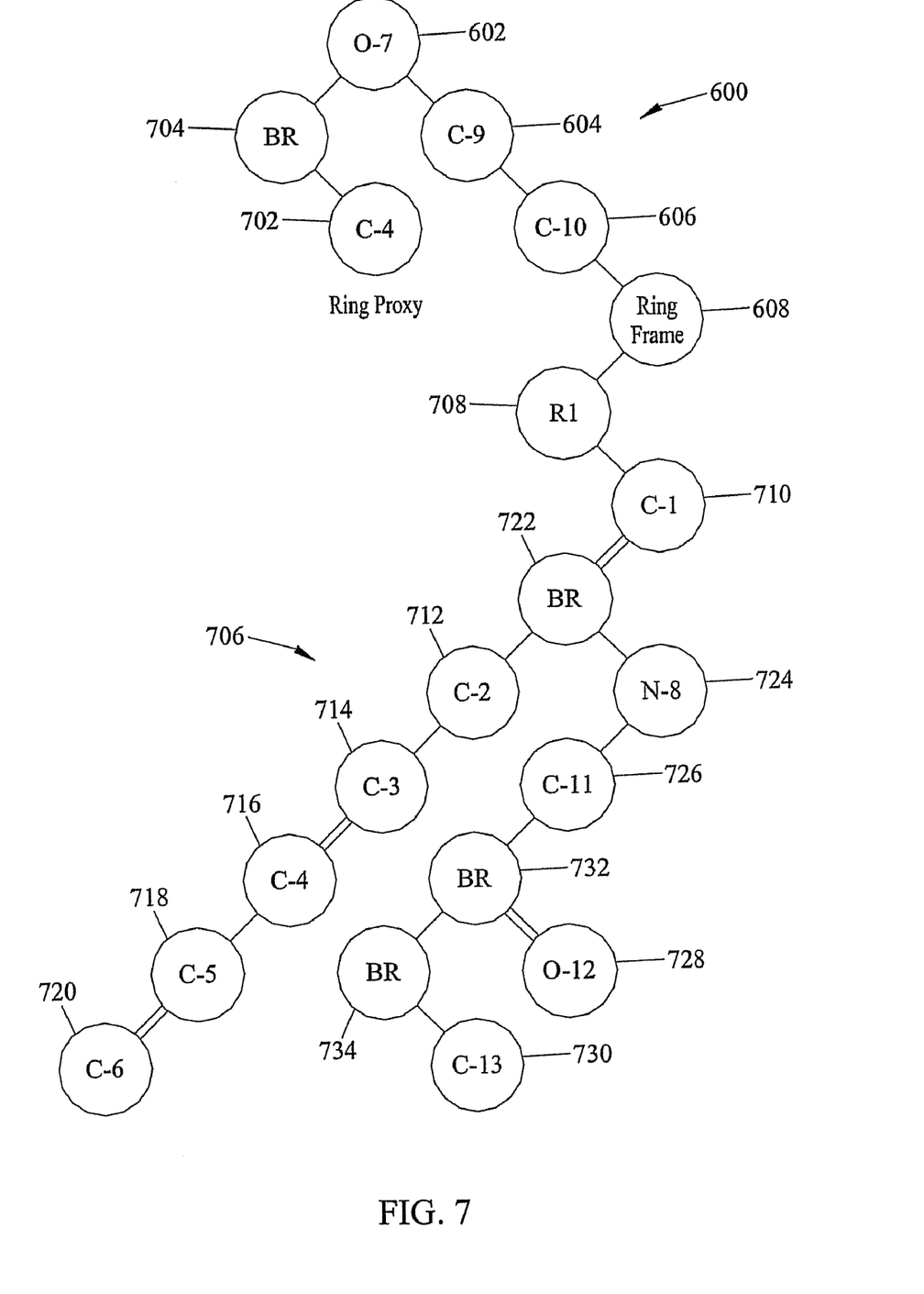
FIG. 7 is a diagram of the completed tree structure for phenacetin.

FIG. 7 is a diagram of the completed tree structure for phenacetin. Beginning with the root node 602, the connectivity list of each atom node in the tree frame 600 is examined. Referring to Table 1, atom node 602, which corresponds to atom #7 in the atom list, has a bond with atom #9 and atom #4. Atom #9 is already represented in the tree by atom node 604. However, an atom node 702 representing atom #4 needs to be added. Applying the node placement rules, in particular the parent atom node rule discussed above with respect to FIG. 5A, atom node 702 cannot be placed as the left-child node of atom node 602. Rather, a branch node 704 is placed as the left-child node of atom node 602, and atom node 702 is placed as the right-child node of branch node 704 according to the parent branch node rule discussed above with reference to FIG. 5C. It should be appreciated that atom #4 is also a member of ring #1. Thus, atom node 702 is identified as a ring-proxy atom node.

For each ringframe node 608 in tree frame 600, a ring tree 706 is generated from the corresponding ring list. Ring tree 706 extends from a ring node 708 and is made up of a series of atom nodes 710, 712, 714, 716, 718, and 720 representing each atom in the ring structure. Ring tree 706 may also include branch nodes 722 to connect atoms in the ring to atoms outside the ring. If the ring is fused to other rings, ring trees for the attached rings are generated. In FIG. 7, branch node 722 connects atom node 724, which represents non-ring atom #8, to atom node 710, which represents ring atom #1. Atom node 726, representing atom #11, is the left-child node of atom node 724. Atom nodes 728 and 730 are connected to atom node 726 via branch nodes 732 and 734, respectively. In FIG. 7, double lines between nodes are used to denote double bonds between atoms.

If the tree frame is generated from the chain list, it is possible that some ring trees may not have been added during atom node processing of the tree frame. Once all nodes in the tree frame have been processed, a final pass is made to add any missing ring trees (i.e., ringframe nodes and their subtrees) to the tree frame and to ensure that the tree structure is complete.

Once the tree structure is built, the process of determining theoretical mass spectrometry fragmentation patterns of the chemical structure begins. Beginning with the root node, a set of fragmentation rules is applied to each node to determine whether the link between the parent node and its left- or right-child node should be broken. The breaking rules are divided into categories, with different rules applying to links between nodes in the tree frame, links between nodes in a left subtree, and links between nodes in a ring. Table 4 lists exemplary breaking rules for links between nodes in the tree frame.

TABLE 4

Exemplary Breaking Rules for Nodes in a Tree Frame

| Category | Parent | Child | Link | Rule |
| --- | --- | --- | --- | --- |
| Frame | RingFrame | RingFrame | Right | No break. |
| Frame | Atom | RingFrame | Right | No break. |
| Frame | Atom | Atom | Right | Break if parent and child single-bonded and [parent has left subtree or child has left subtree or parent is heteroatom or child is heteroatom]. |

In Table 4, the "Link" column indicates whether a rule applies to the right child or left child of the parent node. Since the rules in Table 4 apply to nodes in the tree frame and nodes in the tree frame have a parent-right-child relationship, each rule in Table 4 may apply to a link between a parent node and a right-child node. As shown in Table 4, the only links in the tree frame that may be broken are links between atom nodes. If the link between the atom nodes is a single bond and either atom node has a left subtree or either atom is a heteroatom, then the link is broken, creating two fragments. As used herein, a heteroatom is any atom other than carbon (C) or hydrogen (H). Applying the tree frame fragmentation rules to the tree in FIG. 7, the link between atom node 602 and atom node 604 may be broken while the remaining links between nodes in the tree frame 700 remain intact.

Table 5 lists exemplary breaking rules for links involving nodes in the left subtree. In Table 5, the "Link" column indicates whether the child is the right child or left child of the parent node.

TABLE 5

Exemplary Breaking Rules for Nodes in Left Subtree

| Category | Parent | Child | Link | Rule |
| --- | --- | --- | --- | --- |
| Subtree | RingFrame | Ring | Left | No break. |
| Subtree | Ring | Atom | Right | No break. |
| Subtree | Atom | Atom | Left | Break if not in a ring and parent and child single-bonded and [parent is heteroatom or child is heteroatom or child's left child is branch node]. |
| Subtree | Atom | Branch | Left | No break. |
| Subtree | Branch | Branch | Left | No break. |
| Subtree | Branch | Atom | Left | No break. |
| Subtree | Branch | Atom | Right | Break if grandparent (atom above Branch) and child are single-bonded or if child is ring-proxy. |

As shown in Table 5, links between nodes in a left subtree can be broken in two cases. In one case, a link between a parent atom node and a left-child atom node may be broken if the link is not part of a ring tree, the link represents a single bond, and either the parent or child atom node represents a heteroatom, or the child node has a left-child node that is a branch node. In another case, a link between a parent branch node and a right-child atom node may be broken if the parent of the branch node is an atom node and the link between the branch node and right-child atom node represents a single bond or if the child node is a ring-proxy node. Applying the subtree fragmentation rules to the tree in FIG. 7, the links between the following nodes are broken in turn: branch node 704 and ring-proxy node 702; atom node 724 and atom node 726; and branch node 734 and atom node 730.

Links involving nodes in a ring may be broken by applying the subtree rules in Table 5 and then by applying a set of breaking rules that apply to rings. For clarity, the ring breaking rules are described in terms of the chemical structure rather than tree node relationships.

Figure 8:
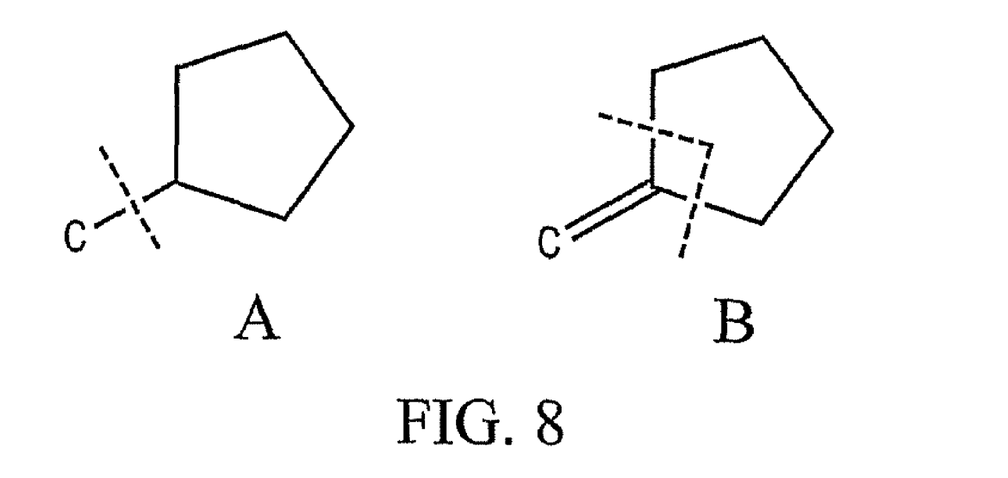
FIGS. 8A and 8B are diagrams illustrating exemplary breaking rules for a link between a non-heteroatom and a ring.

FIGS. 8A and 8B are diagrams illustrating exemplary breaking rules for a link between a non-heteroatom and a ring. As shown in FIG. 8A, if a single bond connects the non-heteroatom, in this case carbon, to the ring, then the bond between the non-heteroatom and the ring may be broken, as denoted by the dashed line in FIG. 8A. However, if a double or triple bond connects the non-heteroatom to the ring, then the ring is broken immediately around the ring atom, as shown in FIG. 8B.

Figure 9:
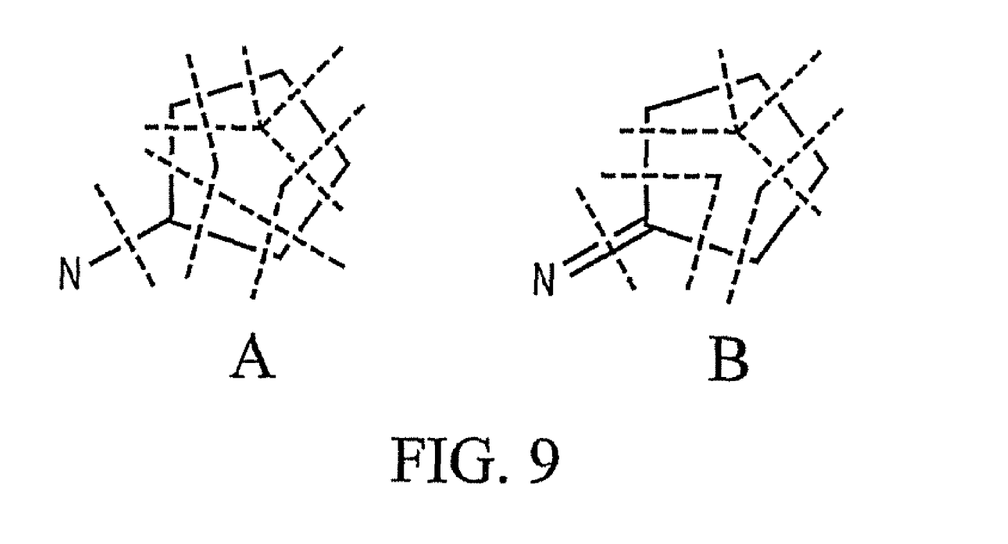
FIGS. 9A and 9B are diagrams illustrating exemplary breaking rules for a link between a heteroatom and a ring.
Figure 10:
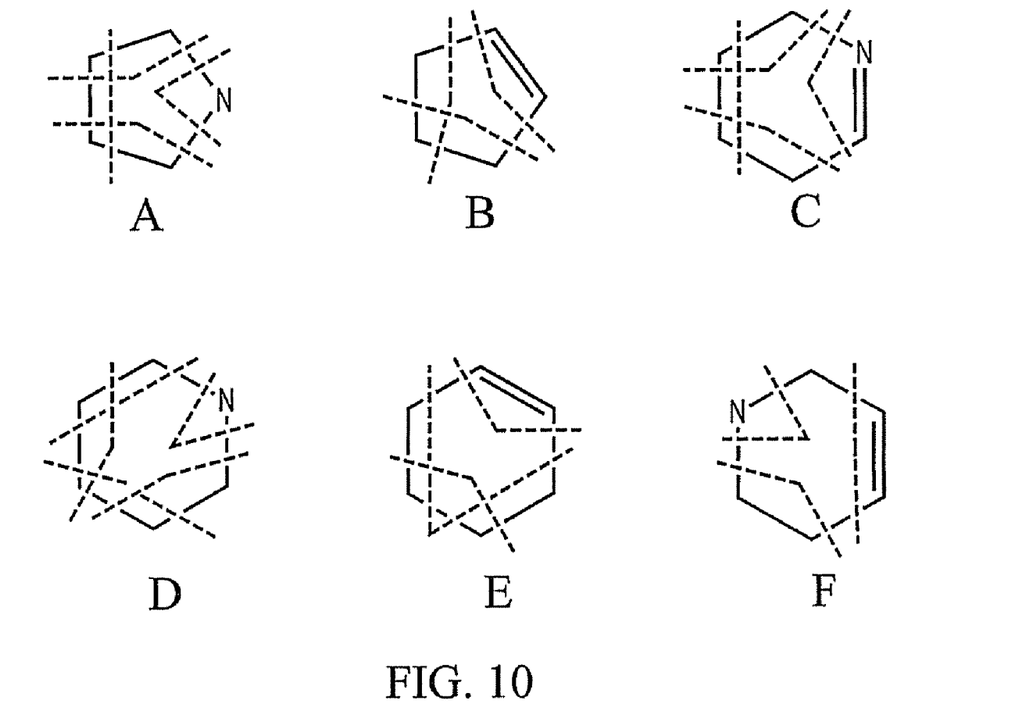
FIGS. 10A-10F are diagrams illustrating exemplary rules for breaking exemplary ring structures.

FIGS. 9A and 9B are diagrams illustrating exemplary breaking rules for a link between a heteroatom and a ring. As shown in FIGS. 9A and 9B, a bond between the heteroatom and the ring should always be broken, regardless of whether the bond is a single, double, or triple bond. In addition, if a single bond connects the heteroatom to the ring, then the ring may be broken in adjacent pairs. In FIG. 9A, the dashed lines indicate six fragments: one between the heteroatom and the ring and five sets of adjacent paired ring atoms. If a double or triple bond connects the heteroatom to the ring, then the ring may be broken immediately around the ring atom bonded to the heteroatom. The remaining portions of the ring may be broken in adjacent pairs. In FIG. 9B, the dashed lines indicate five fragments: one between the heteroatom and the ring, another separating the ring atom bonded with the heteroatom from the rest of the ring, and three sets of adjacent paired ring atoms.

Figure 11:
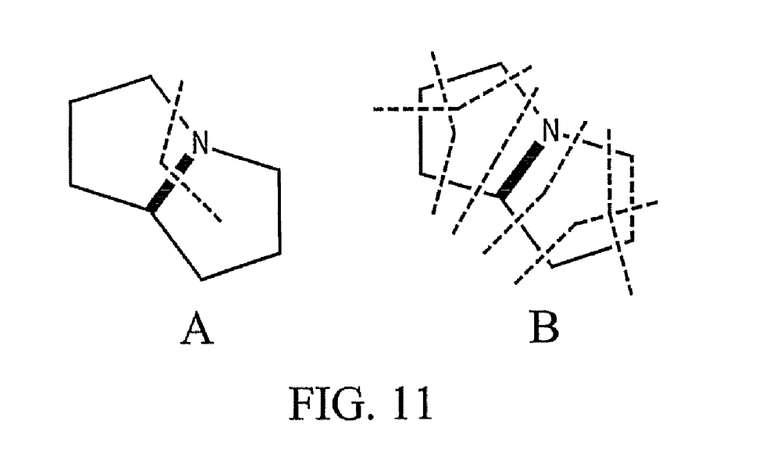
FIGS. 11A and 11B are diagrams illustrating the correct and incorrect application of ring breaking rules as applied to fusion points.

FIGS. 10A-10F are diagrams illustrating exemplary rules for breaking exemplary ring structures. If the ring contains one or more heteroatoms, for example as shown in FIGS. 10A, 10C, 10D, and 10F, the ring should be broken immediately around the heteroatom and around the rest of the ring in adjacent pairs. Double/triple bonds, such as those shown in FIGS. 10B, 10C, 10E, and 10F, should not be broken. Likewise, a fusion point between fused ring structures, as shown in FIG. 11B, should not be broken. FIG. 11A shows an incorrect application of ring breaking rules applied to ring fusion points.

If the link is to be broken, two fragments are generated. One fragment represents the child node and its subtree. The other fragment represents the rest of the tree (the complement). Each fragment may be identified by a string of atom names and numbers. Once the identity of the fragment and the complement have been recorded, the two fragments are reunited in preparation for the next break.

When a break is identified, multiple passes are made through the tree in order to create the fragment and complement strings. In the first pass, which involves only the subtree corresponding to the fragment, the 'fragment type' field in each node of the subtree is set to FRAGMENT. In the next pass, which involves the entire tree, the fragment type is set to COMPLEMENT for all nodes with fragment type not yet set. In the third pass, the complement string is constructed from all nodes marked COMPLEMENT, and in the final pass the fragment string is constructed from all nodes marked FRAGMENT. The fragment type in each node is cleared after the strings have been generated, in preparation for the next break.

In an embodiment of the subject matter described herein, a data structure may be used to represent each fragment. The data structure may be defined in C or C++ as follows.

```
typedef struct_fragment
{
    int             nFragNumber;        // fragment number
    int             nFragType;          // fragment type
    CString         sFrag;              // fragment string with atom
                                        // numbers
    CString         sFragStrip;         // fragment string without
                                        // atom numbers
    CString         sFormula;           // molecular formula
    double          dMWeight;           // molecular weight
    FRAGATOMLIST    vecAtoms;           // list of fragment
                                        // atoms (list of
                                        // FragAtom structs)
} Fragment;
```

The data structure may include seven elements: a fragment number (nFragNumber), which is shared by a fragment and its complement; a fragment type (nFragType), either "fragment" or "complement" that, along with the fragment number, identifies a fragment/complement pair; a fragment string with embedded atom numbers (sFrag); a fragment string without atom numbers (sFragStrip); the molecular formula corresponding to the fragment string (sFormula); the molecular weight of the fragment (dMWeight); and a list of fragment atoms (vecAtoms). Each fragment atom is described using another data structure, which may be defined in C or C++ as follows.

```
typedef struct_fragatom
{
    int         nAtomNumber;    // the atom number
    CString     sAtomName;      // the atom name
    BONDLIST    vecBond;        // list of intact bonds
    BONDLIST    vecBondBroken;  // list of broken bonds
} FragAtom;
```

The data structure may include four elements: an atom number (nAtomNumber), an atom name (sAtomName), a list of bonds (vecBonds) between the atom and other atoms in the fragment (i.e., intact bonds), and a list of bonds (vecBondBroken) between the atom and other atoms not in the fragment (i.e., broken bonds). Each bond (broken or unbroken) is described using another data structure, which may be defined in C or C++ as follows.

```
typedef struct_bondatom
{
    int     nAtomNumber;    // the atom number
    int     nBondType;      // bond type
} BondAtom;
```

The data structure has two elements: an atom number (nAtomNumber) and a bond type (nBondType). The bond type identifies whether the bond is a single bond, a double bond, or a triple bond.

As each fragment is identified, information about the fragment may be stored in a data structure for later use. An exemplary data structure may be defined in C or C++ as follows.

```
typedef struct_fraginfo
{
    FRAGMENTLIST    vecFragment;    // list of all fragments
                                    // (list of Fragment
                                    // structs)
    FRAGMWLIST      vecMWeight;     // list of unique
                                    // molecular weights
                                    // (list of dbls)
    FRAGATOMLIST    vecAllAtoms;    // list of all atoms
                                    // (list of FragAtom
                                    // structs)
} FragInfo;
```

The data structure includes three list elements. The first list element, vecFragment, includes a list of fragment data structures, which have been described above. The second list element, vecMWeight, includes a list of unique molecular weights. The molecular weight of each fragment is calculated and the unique molecular weights are stored in vecMWeight. It should be appreciated that more that one fragment may have the same molecular weight. Thus, the number of unique molecular weights may be less than the number of fragments. The third list element, vecAllAtoms, includes a list of all atoms in the molecular structure and their bonds with each other.

After the tree has been completely traversed and the initial fragment list has been generated, post processing may be performed on the list. Post processing may result in the modification of existing fragments and/or the generation of additional fragments. Examples of post-processing steps may include identifying fragments containing a single-connected, single-bonded oxygen atom and for each such fragment, generating a new fragment identical to the original but without the oxygen atom and with one less hydrogen than would normally appear in the corresponding molecular formula. Another post processing step may include identifying fragments containing one nitrogen atom (i.e. the entire fragment is a nitrogen atom), where the nitrogen atom is single-connected and single-bonded in the molecule (not the fragment), adding an extra hydrogen atom to the fragment's molecular formula (e.g., changing the formula from $NH_2$ to $NH_3$), and modify the fragment's complement by removing one hydrogen from the complement's molecular formula.

Table 6 lists the various fragments of phenacetin. In Table 6, the "Rule" column lists the category of the rule used to create the fragment and its complement. As discussed above, fragmentation rules are applied to the tree frame (frame), left subtrees (subtree), and rings (ring). Table 6 also includes a rule notation for post processing rules, which generate a fragment without a complement.

TABLE 6

Fragments of Phenacetin

| Rule | Fragment String | Stripped Fragment String | Molecular Formula | Molecular Weight |
|---|---|---|---|---|
| Full | C9-C10-O7-C4-C5-C6-C1-C2-C3-N8-C11-O12-C13 | CCOCCCCCCNCOC | $C_{10}H_{14}NO_2$ | 180.1025 |
| Frame | C9-C10 | CC | $C_2H_5$ | 29.0391 |
|  | O7-C4-C5-C6-C1-C2-C3-N8-C11-O12-C13 | OCCCCCCNCOC | $C_8H_8NO_2$ | 150.0555 |
| Subtree | O7-C9-C10 | OCC | $C_2H_5O$ | 45.0340 |
|  | C1-C2-C3-C4-C5-C6-N8-C11-O12-C13 | CCCCCCNCOC | $C_8H_8NO$ | 134.0606 |

TABLE 6-continued

Fragments of Phenacetin

| Rule | Fragment String | Stripped Fragment String | Molecular Formula | Molecular Weight |
|---|---|---|---|---|
| Subtree | C11-O12-C13 | COC | $C_2H_3O$ | 43.0184 |
|  | N8-C1-C2-C3-C4-C5-C6-O7-C9-C10 | NCCCCCCOCC | $C_8H_{10}NO$ | 136.0762 |
| Subtree | C13 | C | $CH_3$ | 15.0235 |
|  | C11-O12-N8-C1-C2-C3-C4-C5-C6-O7-C9-C10 | CONCCCCCOCC | $C_9H_{10}NO_2$ | 164.0712 |
| Ring | N8-C11-O12-C13 | NCOC | $C_2H_4NO$ | 58.0293 |
|  | C1-C2-C3-C4-C5-C6-O7-C9-C10 | CCCCCCOCC | $C_8H_9O$ | 121.0653 |
| Ring | C1-C2-N8-C11-O12-C13 | CCNCOC | $C_4H_6NO$ | 84.0449 |
|  | C3-C4-C5-C6-O7-C9-C10 | CCCCOCC | $C_6H_9O$ | 97.0653 |
| Ring | C3-C4-O7-C9-C10 | CCOCC | $C_4H_7O$ | 71.0497 |
|  | C1-C2-C5-C6-N8-C11-O12-C13 | CCCCNCOC | $C_6H_8NO$ | 110.0606 |
| Ring | C5-C6 | CC | $C_2H_3$ | 27.0235 |
|  | C1-C2-C3-C4-N8-C11-O12-C13-O7-C9-C10 | CCCCNCOCOCC | $C_8H_{12}NO_2$ | 154.0868 |
| Post | C9-C10 | CC | $C_2H_4$ | 28.0313 |
| Post | C4-C5-C6-C1-C2-C3-N8-C11-O12-C13 | CCCCCCNCOC | $C_8H_7NO$ | 133.0528 |

The "Fragment String" column in Table 6 lists the atom name and number of each atom in the fragment. The hyphen used to separate each atom is inserted in Table 6 to provide clarity, but may not be included in the fragment name stored in the sFrag element of the fragment data structure described above. The "Stripped Fragment String" column in Table 6 provides a list of atoms in the fragment without the associated atom numbers and may be used, for example, to determine the molecular formula of the fragment, shown in the "Molecular Formula" column of Table 6. As previously noted, hydrogen atoms are not explicitly shown in the molecular structure or in the fragment strings. In order to determine the molecular formula for a fragment, therefore, the proper number of hydrogen atoms needs to be determined. In one embodiment, the number of hydrogen atoms may be calculated using the following algorithm, written in C or C++.

```
{
    int nH = 0;    // nH stores the number of hydrogens
    nH += (((nC + nSi)*2)+2);    // account for C and Si
    nH += nN + nP;                // account for N and P
    nH -= nF + nBr + nI + nCl;    // account for F, Br, I, and Cl
    nH -= (2*nDoubleBond);        // account for double bonds
    nH -= (4*nTripleBond);        // account for triple bonds
    nH -= (2*nRing);              // account for rings
    if( bFragment )               // account for fragment
        nH--;                     // a fragment/complement
    else
        nH++;                     // entire structure
}
```

The algorithm initializes the variable used to store the number of hydrogen atoms (nH). For example, two hydrogen atoms are added for each carbon (C) or silicon (Si) atom and one hydrogen atom is added for each nitrogen (N) or phosphorus (P) atom. As another example, one hydrogen atom is subtracted for each fluorine (F), bromine (Br), chlorine (Cl), or iodine (I) atom. The number of hydrogen atoms also may be reduced according to the number of double bonds, triple bonds, and rings in the fragment or molecule. If number of hydrogen atoms is being calculated for a fragment, the number of hydrogen atoms is decreased by one. Otherwise, the number of hydrogen atoms is increased by one.

In Table 6, a hydrogen atom has been added to the phenacetin molecule to create a fragment representing the entire molecule. In addition, three fragments each consist of two carbon atoms, but the molecular formula is different for each. One CC fragment, representing C9-C10 and formed by applying the tree frame fragmentation rules, has a molecular formula of $C_2H_5$. Another CC fragment, representing C5-C6 and formed by applying the ring fragmentation rules, has a molecular formula of $C_2H_3$, due to the double bond between the carbon atoms. The third CC fragment, representing C9-C10 and formed by applying post-processing rules to the O7-C9-C10 fragment, has a molecular formula of $C_2H_4$. This fragment was formed by removing an oxygen atom and a hydrogen atom from the O7-C9-C10 fragment.

The subject matter described herein provides methods for producing theoretical mass spectral fragmentation patterns of chemical structures. The subject matter described herein further provides methods for identifying one or more unknown analytes by comparing and matching the theoretical mass spectra with experimentally derived mass spectra of the analytes in order to identify or otherwise characterize the one or more unknown analytes.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A method for generating theoretical mass spectral fragmentation patterns of a chemical structure comprising:
   (a) obtaining a description of a chemical structure;
   (b) generating, from the description, a list of chemical structure information by:
      (i) designating an atom node in a non-ring chain as a root node;
      (ii) building a tree frame extending from the root node wherein each node in the tree frame corresponds to an atom in the non-ring chain and wherein adjacent atoms in the non-ring chain have a parent—right-child node relationship in the tree frame; and,
      (iii) generating a left-child subtree for each node in the tree frame;
   (c) inputting the list of chemical structure information from step (b) into a tree generator, and using the tree generator to execute computer executable instructions to organize the list in a binary tree data structure; and
   (d) inputting the binary tree data structure from step (c) into a tree fragmenter, and using the tree fragmenter to execute computer executable instructions to apply predetermined breaking rules to nodes in the binary tree data structure to identify theoretical mass spectral fragmentation patterns of the chemical structure.

2. The method of claim 1, wherein obtaining the description of the chemical structure includes:
   (a) obtaining a list of atoms in a molecule; and
   (b) obtaining a list of bonds between atoms.

3. The method of claim 1, wherein generating a list of chemical structure information includes:
(a) generating a list of atoms in the chemical structure;
(b) generating a list of rings in the chemical structure; and
(c) generating a list of chains in the chemical structure.

4. The method of claim 3, wherein generating a list of atoms in the chemical structure includes:
(a) generating, for each atom, a connectivity list identifying connecting bonds to other atoms in the list of atoms; and
(b) generating a ring list identifying rings that include the atom.

5. The method of claim 3, wherein generating a list of rings in the chemical structure includes generating, for each ring, a list of atoms that form the ring.

6. The method of claim 3, wherein generating a list of chains in the chemical structure includes:
(a) generating, for each chain, a list of atoms that form the chain; and
(b) identifying the chain having the largest number of non-ring atoms.

7. The method of claim 1, wherein generating a left-child subtree for each node in the tree frame includes:
(a) examining a connectivity list identifying atoms having a bond with the node;
(b) determining, for each atom in the connectivity list, whether the atom is represented in the tree structure; and
(c) in response to determining that the atom is not represented in the tree structure, creating a branch subtree related to the parent node as a left-child node.

8. The method of claim 1 wherein the tree fragmenter applies predetermined breaking rules by:
(a) determining, based on the breaking rules, a fragmentation point between two nodes in the binary tree data structure thereby dividing the binary tree data structure into a fragment and a complement;
(b) determining a molecular formula and a molecular weight for the fragment and storing the molecular formula and molecular weight in a fragment list;
(c) determining a molecular formula and a molecular weight for the complement and storing the molecular formula and molecular weight in the fragment list; and
(d) repeating steps (a)-(c) for each rule in the set of breaking rules.

9. A method for generating theoretical mass spectral fragmentation patterns of a chemical structure comprising:
(a) obtaining a description of a chemical structure;
(b) generating, from the description, a list of chemical structure information by:
(i) designating a ringframe node as a root node; and
(ii) generating a left-child subtree for each ringframe node in the tree frame, wherein each left-child subtree is formed from atom nodes corresponding to atoms in the ring represented by the ringframe and each atom node is related to an adjacent atom node as a left-child node;
(c) inputting the list of chemical structure information from step (b) into a tree generator, and using the tree generator to execute computer executable instructions to organize the list in a binary tree data structure; and
(d) inputting the binary tree data structure from step (c) into a tree fragmenter, and using the tree fragmenter to execute computer executable instructions to apply predetermined breaking rules to nodes in the binary tree data structure to identify theoretical mass spectral fragmentation patterns of the chemical structure.

10. The method of claim 9, wherein obtaining the description of the chemical structure includes:
(a) obtaining a list of atoms in a molecule; and
(b) obtaining a list of bonds between atoms.

11. The method of claim 9, wherein generating a list of chemical structure information includes:
(a) generating a list of atoms in the chemical structure;
(b) generating a list of rings in the chemical structure; and
(c) generating a list of chains in the chemical structure.

12. The method of claim 11, wherein generating a list of atoms in the chemical structure includes:
(a) generating, for each atom, a connectivity list identifying connecting bonds to other atoms in the list of atoms; and
(b) generating a ring list identifying rings that include the atom.

13. The method of claim 11, wherein generating a list of rings in the chemical structure includes generating, for each ring, a list of atoms that form the ring.

14. The method of claim 11, wherein generating a list of chains in the chemical structure includes:
(a) generating, for each chain, a list of atoms that form the chain; and
(b) identifying the chain having the largest number of non-ring atoms.

15. The method of claim 9, wherein generating a left-child subtree for each node in the tree frame includes:
(a) examining a connectivity list identifying atoms having a bond with the node;
(b) determining, for each atom in the connectivity list, whether the atom is represented in the tree structure; and
(c) in response to determining that the atom is not represented in the tree structure, creating a branch subtree related to the parent node as a left-child node.

16. The method of claim 9 wherein the tree fragmenter applies predetermined breaking rules by:
(a) determining, based on the breaking rules, a fragmentation point between two nodes in the binary tree data structure thereby dividing the binary tree data structure into a fragment and a complement;
(b) determining a molecular formula and a molecular weight for the fragment and storing the molecular formula and molecular weight in a fragment list;
(c) determining a molecular formula and a molecular weight for the complement and storing the molecular formula and molecular weight in the fragment list; and
(d) repeating steps (a)-(c) for each rule in the set of breaking rules.

* * * * *